(12) United States Patent
Mason

(10) Patent No.: US 6,260,890 B1
(45) Date of Patent: Jul. 17, 2001

(54) TUBING CONNECTOR

(75) Inventor: Jeffrey T. Mason, Escondido, CA (US)

(73) Assignee: Breg, Inc., Vista, CA (US)

( * ) Notice: Subject to any disclaimer, the term of this patent is extended or adjusted under 35 U.S.C. 154(b) by 0 days.

(21) Appl. No.: 09/374,703

(22) Filed: Aug. 12, 1999

(51) Int. Cl.[7] .................................................. F16L 25/00
(52) U.S. Cl. .......................................... 285/332; 604/256
(58) Field of Search ................................... 285/332, 339, 285/342, 343, 354; 604/167.01, 167.02, 167.06, 246, 256, 415, 533, 539; 606/198

(56) References Cited

U.S. PATENT DOCUMENTS

| | | | |
|---|---|---|---|
| 3,496,937 | * | 2/1970 | Balson .................................. 604/132 |
| 4,187,848 | * | 2/1980 | Taylor .................................. 604/243 |
| 4,346,703 | * | 8/1982 | Dennehey et al. .................... 604/406 |
| 4,360,024 | * | 11/1982 | Wallace ................................. 604/256 |
| 4,508,367 | * | 4/1985 | Oreopoulos et al. ..................... 285/3 |
| 4,512,766 | * | 4/1985 | Vailancourt ........................... 604/169 |
| 4,690,437 | * | 9/1987 | Anderson, Jr. ........................ 285/356 |
| 5,334,188 | * | 8/1994 | Inoue et al. ........................... 604/283 |
| 5,669,637 | * | 9/1997 | Chitty et al. .......................... 285/342 |
| 5,766,203 | * | 6/1998 | Imran et al. .......................... 606/198 |
| 5,908,405 | * | 6/1999 | Imran et al. ............................ 604/53 |
| 5,951,060 | * | 9/1999 | Fukano et al. ......................... 285/92 |
| 5,984,373 | * | 11/1999 | Fitoussi et al. ........................ 285/92 |

OTHER PUBLICATIONS

Drawing No. 80354: Pediatric Touchy Borst Adapter, Qosina Corp., Feb. 19, 1999.*

* cited by examiner

Primary Examiner—B. Dayoan
Assistant Examiner—Carlos M. Lugo
(74) Attorney, Agent, or Firm—Rodney F. Brown

(57) ABSTRACT

A tubing connector has a body, a tubular member, a compression member, a cap and a coupling. The body has a bore extending through it and a body portion of the tubular member is positioned in the bore of the body with an extension portion of the tubular member extending from the bore of the body. The compression member is fitted in the cap and also has a bore extending through it. The cap is provided with an opening and an orifice which are aligned with the bore of the compression member to define a continuous passageway through the cap. The coupling connectively engages the body with the cap. The tubing connector also optionally includes a coupling element which enables connective engagement of the body with an adjoining member. To use the tubing connector, the flexible tube is threaded through the continuous passageway of the cap and fitted over the extension portion of the tubular member. The cap and the body are then connectively engaged around the extension portion. The body applies a compressive force to the elastically-deformable compression member when engaged with the cap which retains the flexible tube in place while the non-elastically-deformable tubular member prevents the compressive force from collapsing the flexible tube.

23 Claims, 5 Drawing Sheets

TUBING CONNECTOR

TECHNICAL FIELD

The present invention relates generally to medical catheters, and more particularly, to a device for connecting a catheter to an adjoining member of a fluid flowpath.

BACKGROUND OF THE INVENTION

A medical catheter is a small tube generally designed for insertion into a cavity, duct or vessel in the body of a patient. Once in place, the medical catheter enables the injection of a fluid into the body or the withdrawal of a fluid from the body. Alternatively, the medical catheter can establish or maintain the patency of a fluid passageway within the body into which the catheter is placed. As such, catheters have utility for a broad range of medical treatment applications.

An exemplary medical treatment application, wherein a catheter is employed to inject a fluid into the body, is the post-operative treatment of a surgical wound. Upon completion of a surgical procedure, one end of the catheter is maintained internally in the patient at or near the surgical wound site while the opposite end of the catheter extends externally out of the body. The external end of the catheter is fluid communicatively connected to a treatment fluid reservoir or a fluid delivery device, such as an infusion pump, a syringe, or a fluid-filled bladder. Connecting the catheter to the reservoir or delivery device enables the practitioner to deliver a treatment fluid to the wound site. The treatment fluid can be an analgesic to manage post-operative pain or any other type of fluid medication which promotes post-operative healing of the surgical wound site.

A coupling or fitting is generally required at the external end of the catheter to enable serial connection of the catheter to the reservoir or delivery device. However, it is often desirable to maintain the external end of the catheter free from attachment to any such connection means while the opposite internal end of the catheter is being placed at the surgical wound site so that the connection means does not interfere with the catheter placement procedure. In such cases, the connection means is preferably installed on the external end of the catheter after placement of the catheter in the treatment site has been completed. The connection means provides a link in the fluid flowpath between the reservoir or delivery device and the treatment site. In particular, the connection means couples the external end of the catheter with an adjoining member of the fluid flowpath which is typically the outlet of the reservoir or delivery device or the outlet of an extension tube provided in the fluid flowpath between the catheter and the remotely positioned reservoir or delivery device. To achieve effective coupling between the external end of the catheter and the adjoining member, the connection means desirably attaches to the external end of the catheter and has a coupling element which can be mated with a corresponding coupling element of the adjoining member.

The attachment function of the connection means may be performed by a fitting which is secured to the external end of the catheter by compression. However, the catheter must have sufficient girth and rigidity to resist occlusion when subjected to compression. Unfortunately, the characteristics of relatively large diameter and high degree of rigidity are generally undesirable for the post-operative treatment function of the catheter. A catheter having a relatively small diameter is more desirable for the post-operative treatment function because it minimizes disruption of the treatment site and promotes healing. A catheter having a relatively high degree of flexibility is also more desirable for the post-operative treatment function because it permits the catheter to follow a tortuous path with a minimal risk of kinking and blockage of treatment fluid flow. However, if a compression force sufficient to adequately secure the catheter to the connection means is applied to a small diameter, highly flexible tube of the type preferred for use as a medical catheter, the connection means is likely to pinch the catheter resulting in partial or total occlusion of the catheter. Conversely, if the compression force is reduced sufficiently to avoid occlusion of the catheter, the catheter is likely to disengage from the connection means at the point of attachment under the stresses of normal use. Neither likelihood is acceptable if effective post-operative treatment of the surgical wound site is to be achieved.

The present invention recognizes a need for a tubing connector which can be securely, yet releasably, installed on the external end of a small diameter, highly flexible catheter without substantially occluding the catheter or otherwise disrupting fluid flow through the catheter. Accordingly, it is an object of the present invention to provide an effective tubing connector for releasable attachment to an end of a tube. More particularly, it is an object of the present invention to provide a tubing connector which can be securely, yet releasably, installed on the end of a catheter without substantially disrupting fluid flow through the catheter. It is another object of the present invention to provide a tubing connector which can be securely installed on the end of a catheter after the opposite end of the catheter has been placed in a treatment site of a patient. It is yet another object of the present invention to provide a tubing connector which can effectively couple a catheter with an adjoining member of a fluid flowpath. It is still another object of the present invention to provide a tubing connector which can be utilized effectively with a small diameter, highly flexible catheter.

These objects and others are accomplished in accordance with the invention described hereafter.

SUMMARY OF THE INVENTION

The present invention is a tubing connector comprising a body, a tubular member, a compression member, a cap and a coupling. The body, tubular member and cap are substantially resistant to elastic deformation. The body is preferably formed from a non-metallic, non-elastically-deformable material while the tubular member is preferably formed from a metallic, non-elastically-deformable material. The compression member compressively engages the body and the compression member is substantially elastically deformable under the compressive force of engagement with the body. A bore extends through the body and a body portion of the tubular member is positioned in the bore of the body with an extension portion of the tubular member extending from the bore of the body. A bore also extends through the compression member and the extension portion and a flexible tube fitted over the extension portion are positioned in the bore of the compression member. The compression member is fitted within the cap and the bore of the compression member aligns with an opening in the cap and an orifice in the cap to define a continuous passageway through the cap. The opening in the cap has a substantially larger cross-section than the tubular member and the orifice in the cap has a smaller cross-section than the opening. A first coupling element of the coupling is positioned on the cap and a second coupling element of the coupling is positioned on the body to cooperatively engage the body with the cap. The first coupling element is preferably a female thread and the second coupling element is preferably a male thread or vice versa. The tubing connector also optionally comprises a coupling element positioned on the body for coupling an adjoining member and the body to provide fluid communication between the flexible tube fitted over the extension portion and the adjoining member.

In accordance with a method of the present invention, the above-recited tubing connector is used to fluid communicatively connect a flexible tube to an adjoining member. The method comprises threading a portion of the flexible tube through the bore of the compression member and through the opening and orifice of the cap. The body portion of the tubular member is provided positioned in the bore of the body and the extension portion of the tubular member is provided extending from the bore of the body. The portion of the flexible tube threaded through the cap is fitted over the extension portion of the tubular member. The compression member and body are then compressively engaged in selective releasable engagement by threadably engaging the cap and body. Thereafter, the body is coupled with the adjoining member to provide fluid communication between the flexible tube and the adjoining member.

Compressive engagement of the compression member and body elastically deforms the compression member and compresses the compression member against the portion of the flexible tube which is fitted over the extension portion and positioned in the bore of the compression member. The compressive force effectively retains the portion of the flexible tube within the bore of the compression member while the tubular member prevents the compressive force from occluding the flexible tube.

An alternate method for retaining a flexible tube in a tubing connector without substantially occluding the flexible tube is further provided by fitting a portion of the flexible tube over a portion of the tubular member and threading the portion of the flexible tube through the bore in the compression member. The tubular member is positioned in the bore of the body and at least part of the portion of the tubular member and at least part of the portion of the flexible tube are extended from the bore of the body into the bore of the compression member. The compression member is compressively engaged by the body to deform the compression member and retain the at least part of the portion of the flexible tube in the bore of the compression member. In accordance with the present method, the sequence of threading the flexible tube through the bore of the compression member and fitting the flexible tube over the tubular member may be performed in either order. Likewise, the sequence of fitting the flexible tube over the tubular member and positioning the tubular member in the bore of the body may be performed in either order.

The present invention will be further understood from the drawings and the following detailed description.

DESCRIPTION OF PREFERRED EMBODIMENTS

Figure 1:
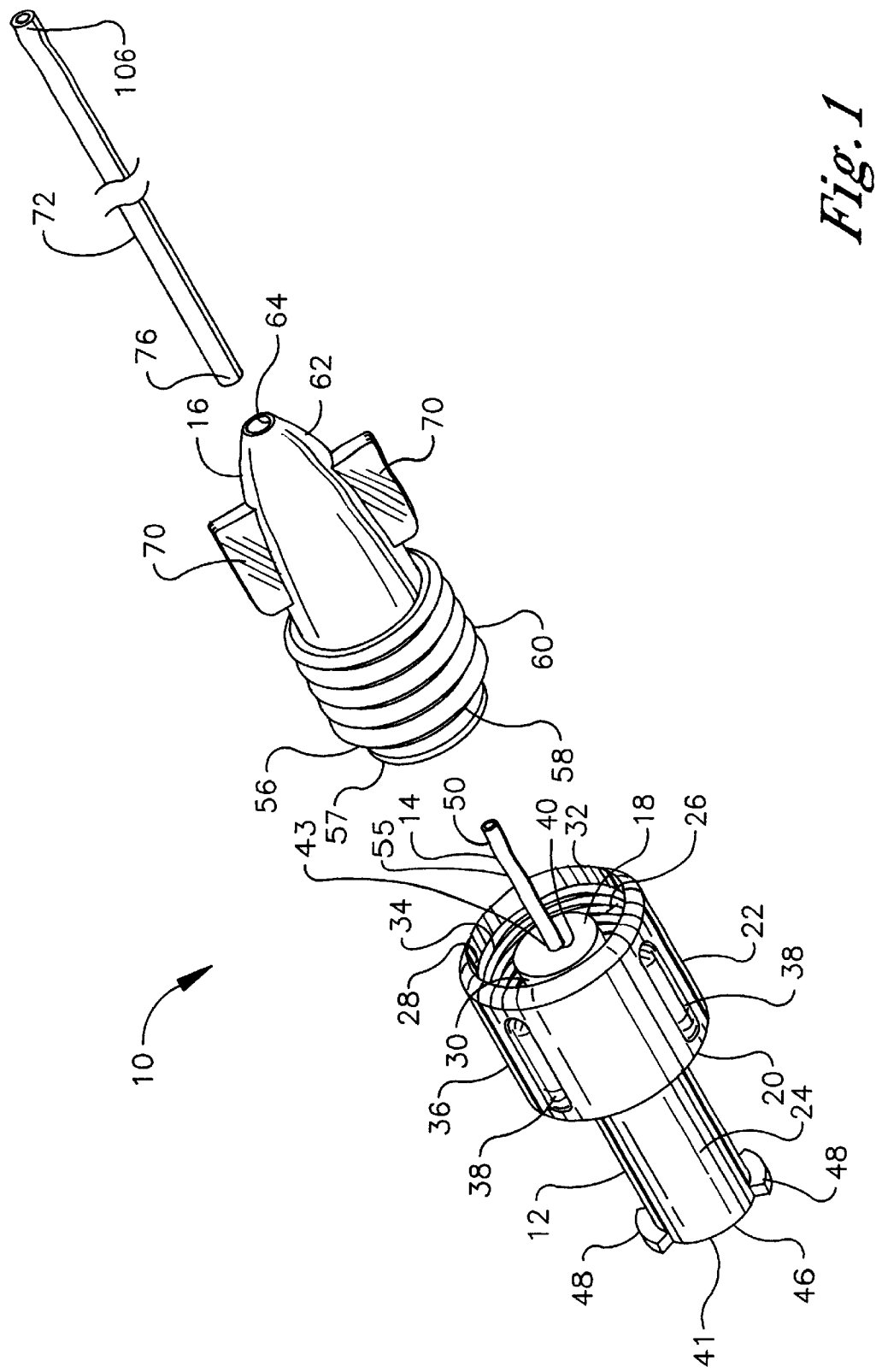
FIG. 1 is an exploded perspective view of a tubing connector of the present invention and an associated catheter.
Figure 4:
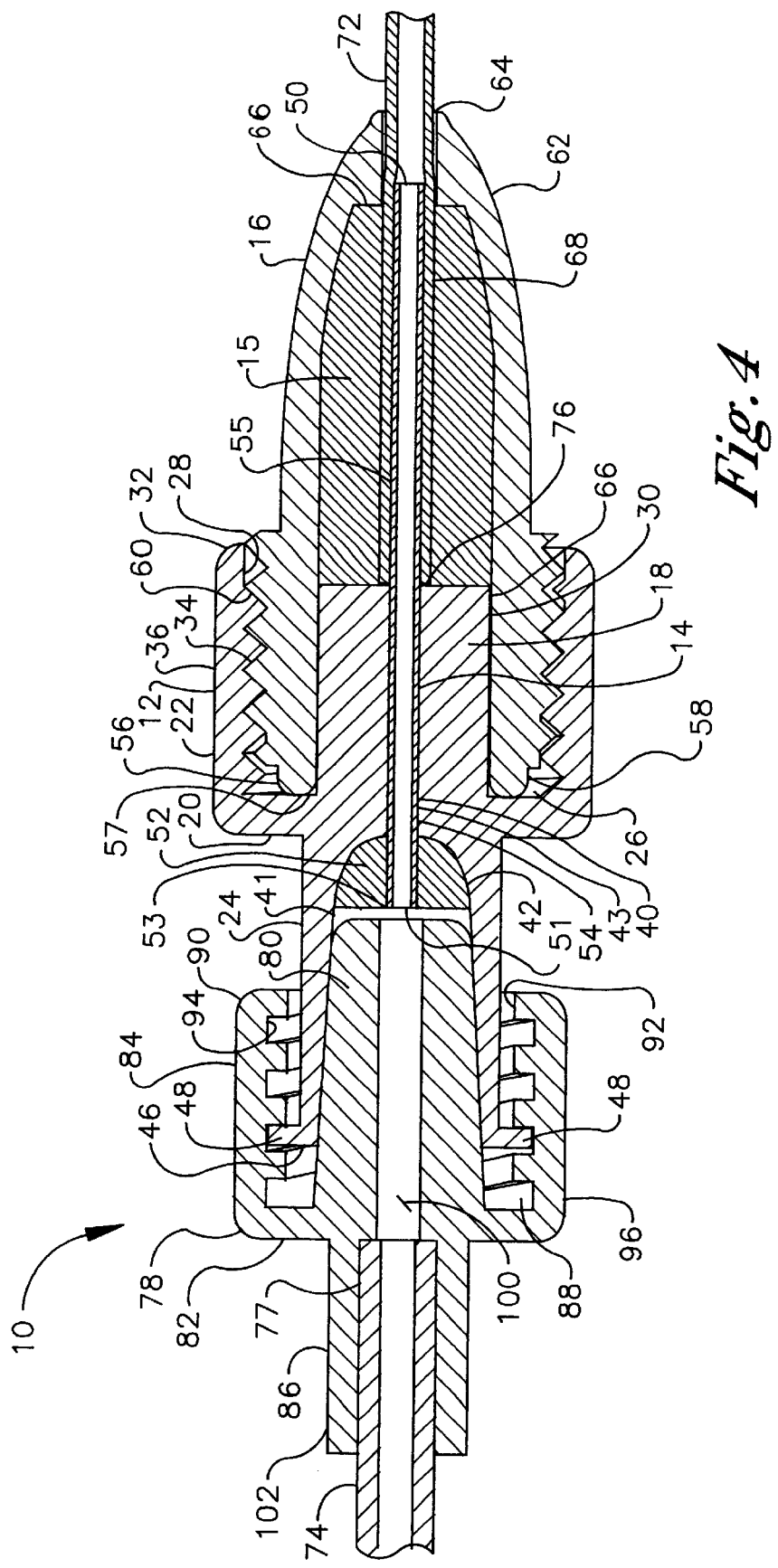
FIG. 4 is a cross-sectional view of the tubing connector of FIG. 3 taken along line 4—4.

Referring initially to FIGS. 1 and 4, a tubing connector of the present invention is shown and generally designated 10. The tubing connector 10 comprises a body 12, a tubular member 14, a compression member 15, and a cap 16. The body 12 is an integral structure comprising a central cylinder 18, a flange 20, a first shroud 22, and a second shroud 24. The flange 20 has a circular configuration and is aligned substantially perpendicular to the longitudinal axis of the tubing connector 10. The first shroud 22 extends longitudinally from the outer periphery of the flange 20 in a first direction which is substantially parallel to the longitudinal axis of the tubing connector and perpendicular to the planar orientation of the flange 20. The first shroud 22 is equidistantly aligned about the longitudinal axis of the body 12, rendering the first shroud 22 concentric with the body 12. The central cylinder 18 likewise extends longitudinally in the first direction, but from the center of the flange 20 along the longitudinal axis of the body 12 concentric with the body 12. The outside diameter of the central cylinder 18 is substantially less than the inside diameter of the first shroud 22, thereby forming an annulus 26 between the inside wall 28 of the first shroud 22 and the outside wall 30 of the central cylinder 18. The central cylinder 18 is slightly shorter in length than the first shroud 22 so that the central cylinder 18 does not substantially extend past the outside edge 32 of the first shroud 22. The inside wall 28 of the first shroud 22 is threaded with a continuous female thread 34 which serves as a first cooperative coupling element. The outside wall 36 of the first shroud 22 has a series of longitudinal ridges 38 formed thereon to facilitate manual gripping and rotating of the body 12.

A continuous central bore 40 extends longitudinally through the body 12 along the longitudinal axis of the body 12 concentric with the body 12. The central bore 40 has a widened section 41 which is substantially enclosed by the second shroud 24. The widened section 41 is followed in series, moving in the first direction, by an intermediately positioned tapered section 42 having a hemispherical or frustaconical configuration which extends to the flange 20, and a uniformly narrowed section 43 which is enclosed by the central cylinder 18. The wall thickness of the central cylinder 18 surrounding the narrowed section 43 is substantially greater than the wall thickness of the first shroud 22.

The second shroud 24 extends longitudinally from the flange 20 in a second direction which is substantially opposite the first direction. The outside diameter of the second shroud 24 approximates the outside diameter of the central cylinder 18. The cross-section of the second shroud 24 is substantially less than that of the first shroud 22, while the length and wall thickness of the second shroud 24 are similar to the length and wall thickness of the first shroud 22. Thus, the second shroud 24 has a more narrow tube-like configuration than the first shroud 22. The second shroud 24, like the first shroud 22, is equidistantly aligned about the longitudinal axis of the body 12 and, thereby, concentric with the body 12. The widened section 41 of the central bore 40 defines the interior of the second shroud 24. The outside edge 46 of the second shroud 24 has a pair of radially-extending tabs 48 formed thereon which serve as a coupling element to enable coupling of the body 12 with an adjoining member. In a preferred embodiment, the body 12 is integrally formed from a strong, durable, rigid plastic, such as a molded polycarbonate or rigid PVC, or some other synthetic nonmetallic material. The material of the body 12 is substantially rigid and inelastic, being highly resistant to elastic deformation and failure.

The tubular member 14 has a tube configuration with the characteristics of a straight, uniform, thin-walled, continuously open cannula having open first and second ends 50 and 51, respectively. The tubular member 14 is extremely strong, durable and rigid throughout its length, preferably formed from a material having at least equal or greater strength, durability and rigidity than the non-metallic material of the body 12. A preferred tubular member 14 is formed from a high-strength metal, such as stainless steel. As such the material of the tubular member 14 is likewise substantially rigid and inelastic, being at least equally or more resistant to elastic deformation and failure than the material of the body 12. The tubular member 14 is fixably positioned within the central bore 40 using an elastic plug 52 formed from a pliant, elastically-deformable material such as a relatively pliant elastomer or silicon rubber. The plug 52 preferably has the configuration of an O-ring or short tubing section provided with a central opening 53.

The tubular member 14 is fixably positioned in the central bore 40 by inserting the second end 51 of the tubular member 14 into the central opening 53 of the plug 52. The first end 50 of the tubular member 14 is then slid through the central bore 40 in the first direction until the plug 52 reaches the tapered section 42. The plug 52 is forcibly pressed into the tapered section 42 compressing the plug 52 against the wall of the tapered section 42 and deforming the outer configuration of the plug 52 to resemble that of the tapered section 42. The compression force of the plug 52 against the wall of the tapered section 42 renders the plug 52, and the tubular member 14 positioned therein, essentially immobile and anchored within the central bore 40. Although not shown, the tubular member 14 may alternatively be secured within the central bore 40 by a bonder, such as a glue or adhesive, and more particularly a UV or epoxy adhesive, applied to the wall of the narrowed section 43. In other alternatives, the tubular member 14 may be secured within the central bore 40 by welding the tubular member 14 to the wall of the narrowed section 43, by insert molding the tubular member 14 in the narrowed section 43, or by press fitting the tubular member 14 into the narrowed section 43. In these alternate cases, the tapered section 42 of the central bore 40 may be omitted, with the central bore 40 transitioning directly from the widened section 41 to the narrowed section 43.

The tubular member 14 is substantially longer than the combined length of the tapered and narrowed sections 42, 43 of the central bore 40. A body portion 54 of the tubular member 14 which is proximal to the open second end 51 resides in the entirety of the combined length of the tapered and narrowed sections 42, 43. An extension portion 55 of the tubular member 14 which is proximal to the open first end 50 extends out of the central bore 40 in the first direction away from the body 12 such that the first end 50 has substantial clearance from the central cylinder 18 and the first shroud 22. The extension portion 55 preferably has a length equal to or somewhat greater than the length of the compression member 15. The open second end 51, as shown, does not extend in the second direction from the tapered section 42 into the widened section 41. However, the second end 51 may extend if desired into the widened section 41, although typically to a lesser degree than the first end 50 extends from the narrowed section 43 in the first direction. In any case, the second end 51 is substantially enclosed by the second shroud 24. As a result, the widened section 41 and tubular member 14, in series, provide a continuous open passageway through the body 12 when the body portion 54 of the tubular member 14 is fixably positioned in the central bore 40.

The cap 16 is an integral structure preferably integrally formed from a strong, durable, rigid plastic which is substantially inelastic, such as the material used to form the body 12. The cap 16 has a first end 56 with an opening 57 encircled by an outside wall 58, wherein the diameter of the outside wall 58 at the opening 57 is slightly less than the diameter of the inside wall 28 of the first shroud 22. The outside wall 58 is threaded with a continuous male thread 60 which serves as a second cooperative coupling element to be fastenably received by the continuous female thread 34 on the inside wall 28 of the first shroud 22. When the outside wall 58 is in threadably fastened engagement with the inside wall 28, the outside wall 58 is received by the annulus 26 and the first end 50 of the tubular member 14 extends through the opening 57 of the cap 16. A second opposite end 62 of the cap 16 tapers to an orifice 64 centrally aligned along the longitudinal axis of the cap 16. The diameter of the orifice 64 is sized larger than the outside diameter of the tubular member 14 to receive the first end 50 of the tubular member 14 therein.

The compression member 15 is shown fifted as an insert into the interior of the cap 16 against the inside wall 66 proximal to the second end 62. The compression member 15 is preferably secured in the interior of the cap 16 by compression fitting or other means such as bonding or the like. The compression member 15 is formed from a substantially non-rigid, pliant, elastically-deformable material, i.e., substantially more elastically deformable than the material of the body 12, tubular member 14 or cap 16 when subjected to the level of compressive forces experienced during use of the tubing connector 10. Latex is an exemplary elastic material from which the compression member 15 may be fabricated, although the present invention is not limited to a specific elastically-deformable material. Alternatively, the compression member 15 may be formed from a substantially rigid inelastic material and provided with mechanical means (not shown) which enable elastic deformation of the compression member 15, such as expansion/contraction slots, grooves or other mechanical means within the purview of the skilled artisan. In any case, the compression member 15 is readily susceptible to physical elastic deformation whereby the compression member 15 elastically changes shape without a substantial change in volume when compressed between the body 12 and the cap 16 in a manner described below.

The compression member 15 has a central bore 68 therethrough which is in serial alignment with the orifice 64. The central bore 68 has a diameter substantially the same as the orifice 64, i.e., greater than the outside diameter of the tubular member 14, to likewise receive the first end 50 of the tubular member 14 therethrough. The outside wall 58 has a pair of tabs 70 formed thereon proximal to the second end 62 to facilitate manual gripping and rotating of the cap 16.

Figure 2:
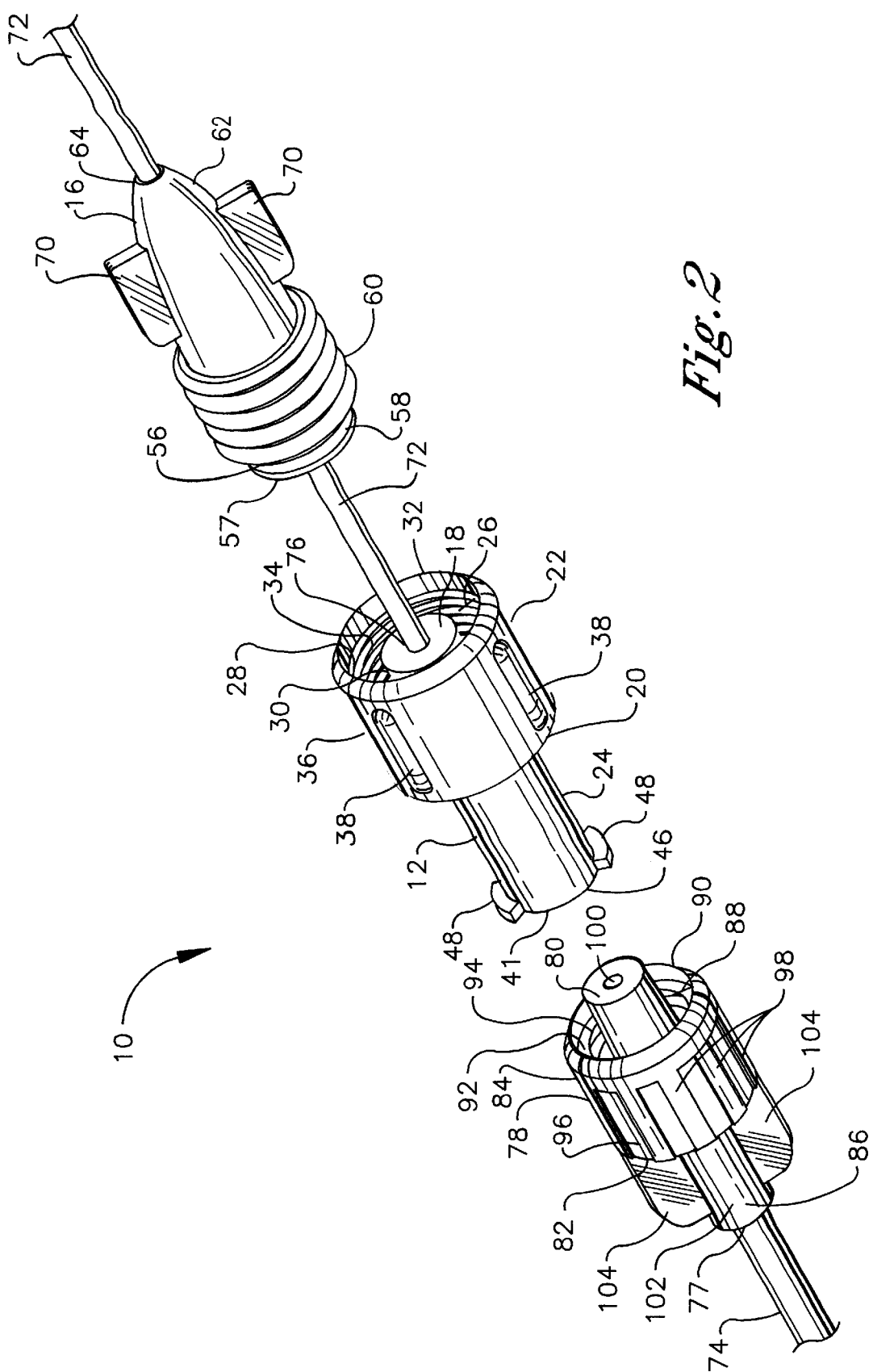
FIG. 2 is an exploded perspective view of the tubing connector of FIG. 1 and an adjoining member, wherein the catheter has been positioned in engagement with the body of the tubing connector.
Figure 3:
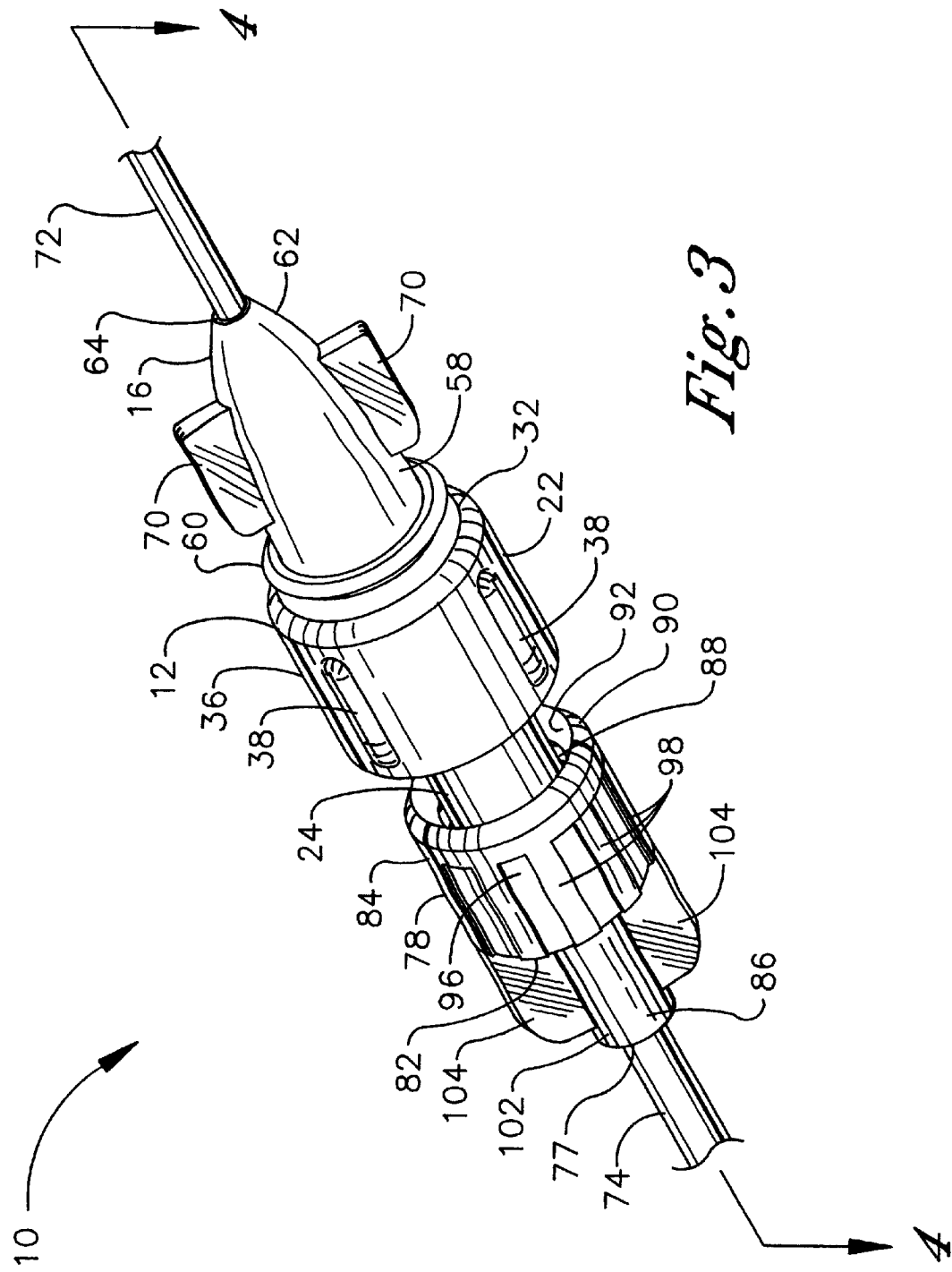
FIG. 3 is a perspective view of the tubing connector of FIG. 2 assembled in association with the catheter and the adjoining member.

Referring additionally to FIGS. 2 and 3, the tubing connector 10 is designed for use in cooperation with an associated tube 72 and an adjoining member 74. The tube 72 shown herein is a clear, flexible, plastic medical catheter 72. However, it is understood that the present invention applies generally to many tube sizes and applications. The present medical catheter 72 is typically a 10 to 20 gauge tubing formed from a material such as nylon or polyurethane. A preferred catheter 72 is a 16 gauge tubing having a relatively small outside diameter of about 0.057 inches, a relatively small inside diameter of about 0.036 inches and a durameter flexibility of about 65D. The adjoining member 74 is shown herein, by way of example, to be a substantially uniform, transparent or translucent, flexible, plastic extension tube. The extension tube 74 is a relatively large vinyl tubing of the type termed in the art as "microbore tubing" which has an outside diameter of about 0.094 inches. The extension tube 74 has a relatively large flow cross-section which enables the rapid displacement of relatively large volumes of liquids through the extension tube 74. It is understood that, within the scope of the present invention, the adjoining member can alternately be other constructs such as the outlet of a treatment fluid reservoir or a fluid delivery device (not shown).

For purposes of illustration, the tubing connector 10 is shown specifically designed for coupling the external end 76 of the catheter 72 with an end 77 of the extension tube 74 by releasably mating the second shroud 24 with a connector 78 mounted on the end 77. To effect attachment of the tubing connector 10 to the external end 76 of the catheter 72, the inside diameter of the orifice 64 and the diameter of the bore 68 are sized larger than the outside diameter of the catheter 72. Thus, the orifice 64 and bore 68 can slidably receive the catheter 72 therethrough. Conversely, the outside diameter of the first end 50 of the tubular member 14 is sized smaller than the inside diameter of the catheter 72 so that the catheter 72 slidably fits over the first end 50.

The connector 78 is an integral structure preferably integrally formed from a durable, rigid plastic, such as the material used to form the body 12 and the cap 16. The connector 78 comprises a central cylinder 80, a flange 82, a shroud 84, and a tubing retainer 86. The central cylinder 80, flange 82 and shroud 84 are configured in a substantially similar manner to the corresponding components 18, 20, 22 of the tubing connector 10. The central cylinder 80 and the shroud 84 form an annulus 88 between them. However, the central cylinder 80 is somewhat longer in length than the shroud 84 so that the central cylinder 80 extends past the annulus 88 and the outside edge 90 of the shroud 84.

The inside wall 92 of the shroud 84 is threaded with a continuous thread 94 which serves as a coupling element. The diameter of the inside wall 90 of the shroud 84 is slightly greater than the diameter of the outside edge 32 of the second shroud 24 of the body 12 so that the second shroud 24 can be received within the annulus 88 of the shroud 84 when the tabs 48 are in threadably fastened engagement with the thread 94. Thus, the second shroud 24 functions in the manner of a female Luer lock fitting to receive the central cylinder 80 and the shroud 84 functions in the manner of a male Luer lock fitting. The outside wall 96 of the shroud 84 has a series of longitudinal ridges 98 formed thereon to facilitate manual gripping and rotating of the connector 78. A continuous narrow central bore 100, having a diameter substantially similar to the diameter of the central bore 40, extends longitudinally through the central cylinder 80 and the flange 82 along the longitudinal axis of the connector 78.

The tubing retainer 86 extends longitudinally from the flange 82 in a direction opposite the shroud 84. The tubing retainer 86 is equidistantly aligned about the longitudinal axis of the connector 78 concentric with the central cylinder 80. The outside wall 102 of the tubing retainer 86 has a pair of tabs 104 formed thereon to facilitate manual gripping and rotating of the connector 78. The interior of the tubing retainer 86 and the central bore 100 provide a continuous open passageway through the connector 78. The inside diameter of the tubing retainer 86 is somewhat less than the outside diameter of the end 77 of the extension tube 74 to receive the extension tube 74 therein. The extension tube 74 is preferably fixably anchored within the tubing retainer 86 by welding, an adhesive, or other fastening means.

The practitioner assembles the tubing connector 10 in association with the catheter 72 and extension tube 74 in accordance with the following procedure. The catheter 72 is initially maintained free from attachment to the tubing connector 10 or any other components as shown in FIG. 1. An internal end 106 of the catheter 72 is placed internally beneath the skin of a patient at or near a treatment site (not shown) preferably by means of an introducer needle and insertion catheter (not shown) in accordance with a technique described in the commonly owned copending U.S. patent application Ser. No. 09/334,856 filed Jun. 16, 1999, entitled "Patient-Controlled Medication Delivery System", which is incorporated herein by reference. The internal end 106 is fixed in the treatment site by securing an adjacent exposed segment of the catheter 72 to the skin of the patient with a strip of tape or other securing means.

The external end 76 of the catheter 72 is manually threaded from the second direction into the orifice 64 in the second end 62 of the cap 16, through the bore 68, and out the opening 57 in the first end 56 with several centimeters of the catheter 72 extending in the second direction from the opening 57. The external end 76 is manually fitted over the first end 50 of the tubular member 14 and the external end 76 is urged in the second direction over the entire length of the extension portion 55 until the external end 76 of the catheter 72 engages the central cylinder 18 as shown in FIG. 2. The cap 16 is slid along the catheter 72 in the second direction toward the body 12 until the thread 60 engages the thread 34. The threads 34, 60 are screwed together positioning the first end 50 of the tubular member 14 in the orifice 64 and bringing the central cylinder 18 into engagement with the compression member 15. The first end 50 of the tubular member 14 preferably does not extend in the first direction beyond the orifice 64 to avoid flexing the catheter 72 over the first end 50 and occluding the catheter 72 during use. As the threads 34, 60 are tightened to complete assembly of the tubing connector 10, the central cylinder 18 engages and elastically deforms the compression member 15 which is countered by the inside wall of the cap 16. By compressing the compression member 15 against the length of the catheter 72 which covers the extension portion 55, the compression member 15 tightly retains the catheter 72 in the tubing connector 10 while the tubular member 14 prevents the compression member 15 from collapsing the catheter 72 within the tubing connector 10. Accordingly, the catheter 72 and tubular member 14 define an occlusion-resistant fluid pathway from the treatment site through the assembled tubing connector 10.

To complete connection of the catheter 72 with the extension tube 74 using the tubing connector 10, the shroud 84 of the connector 78 is placed around the outside edge 46 of the second shroud 24 until the tabs 48 engage the thread 94 of the shroud 84. The shroud 84 is tightened down onto the second shroud 24 by rotating them in opposite directions providing fluid-tight connective engagement between the body 12 and the connector 78 as shown in FIG. 3. The opposite end (not shown) of the extension tube 74 may then be connected to a remote device (not shown) such as an infusion pump described in U.S. patent application Ser. No. 09/334,856.

The tubing connector 10 of the present invention enables the practitioner to employ a catheter 72 having both a relatively small diameter and a relatively high degree of flexibility while securely retaining the catheter 72 and coupling the catheter 72 with an adjoining member 74. The tubing connector 10, and in particular the tubular member 14 and compression member 15, allow the application of a higher compressive force to the catheter 72 to more effectively retain the catheter 72 in the tubing connector 10 while at the same time preventing the higher compressive force from substantially occluding, collapsing or otherwise restricting the catheter 72.

Although not shown, a number of alternate embodiments of the above-recited tubing connector 10 are possible within the scope of the present invention. For example, a tubing connector may be constructed which is substantially similar to the tubing connector 10, but wherein the tubular member 14 is not anchored to the body 12 of the tubing connector. In accordance with this embodiment, neither the plug 52 nor any bonders are utilized. The external end 76 of the catheter 72 is manually fitted over the first end 50 of the tubular member 14 while the tubular member 14 is substantially free from the body 12. The external end 76 is urged over the entirety of the tubular member 14 until the external end 76 is flush with the second end 51. The tubular member 14 and external end 76 are then manually threaded through the cap 16. Alternatively the order of assembly is reversed, wherein the external end 76 is threaded through the cap 16 first and then the tubular member 14 is fitted in the external end 76. In either case, the external end 76 having the tubular member 14 fitted therein is positioned in the bores 40, 68, which are sized to receive both the external end 76 and tubular member 14. The cap 16 is secured to the body 12 in substantially the same manner as described above with respect to the previous embodiment. The compressive force of the central cylinder 18 against the compression member 15 retains the tubular member 14 and external end 76 in the bores 40, 68 as long as the cap 16 remains secured to the body 12.

It is further noted that connective engagement of the body 12 with the connector 78 is described above by fitting the second shroud 24 of the body 12 into the shroud 84 of the connector 78. However, it is apparent to the skilled artisan that the configuration of the shrouds 24 and 84 can be reversed so that the shroud of the connector fits into the second shroud of the body. Similarly, connective engagement of the body 12 with the cap 16 is described above by screwing the first end 56 of the cap 16 into the first shroud 22 of the body 12. It is likewise apparent to the skilled artisan that the configuration of the first end 56 and first shroud 22 can be reversed so that the first shroud of the body screws into the first end of the cap. Such adaptations are applicable to all of the above-described embodiments of the invention.

In another embodiment, the body 12 is reconfigured without the tabs 48 on the second shroud 24. In accordance with this embodiment, the second shroud 24 may be configured as a barbed tube fitting to connect the extension tube 74 or other adjoining member directly to the body 12 and obviate the connector 78. Similarly, the second shroud 24 may be configured as a fitting to glue or otherwise bond the extension tube 74 or other adjoining member directly to the body 12 and likewise obviate the connector 78. Alternatively, the second shroud 24 may be integrally formed with an adjoining member so that the body and adjoining member are a single integrated structure. For example, the body 12 could be integrally formed on the outlet of a syringe or infusion pump. In accordance with this embodiment, the second shroud 24 may be retained as is on the body 12, substantially shortened, or completely omitted from the body 12, obviating the widened section 41 of the bore 40 and repositioning the tapered section 42 in the central cylinder 18.

Figure 5:
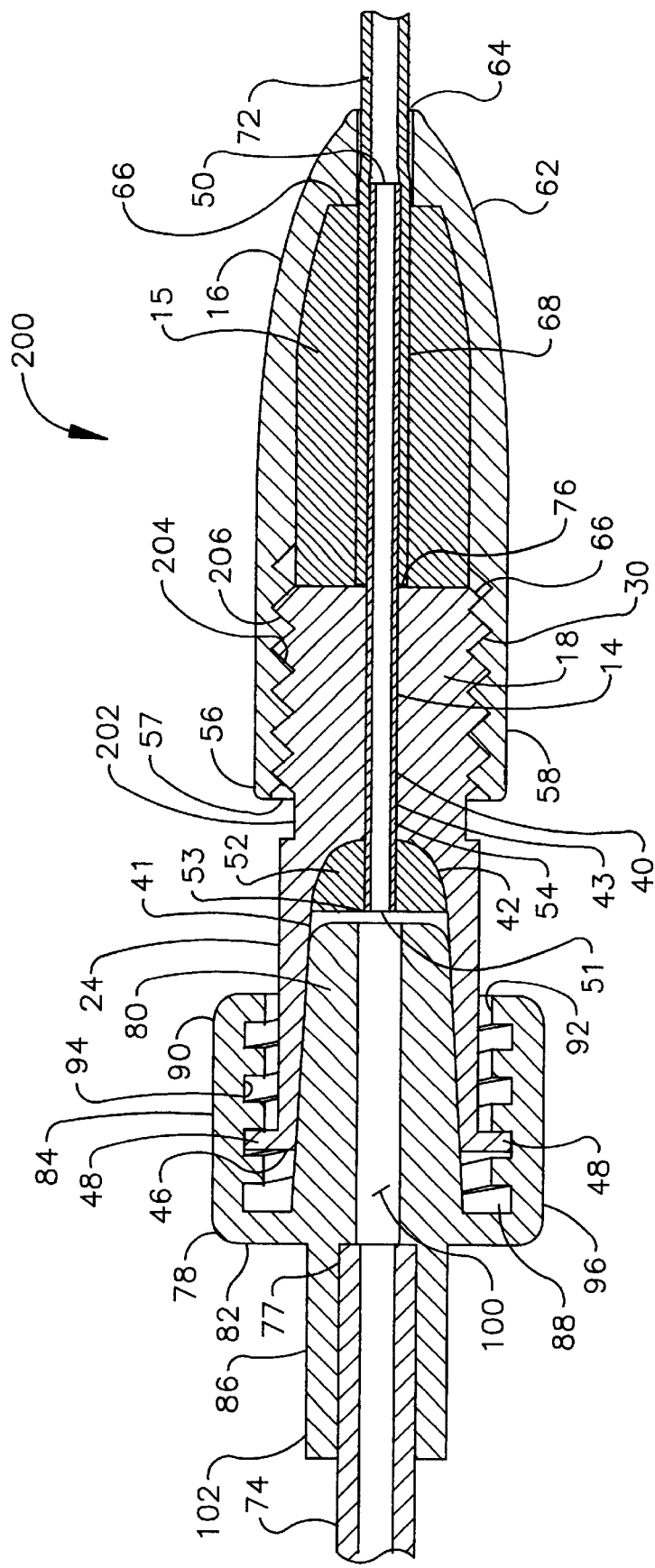
FIG. 5 is a cross-sectional view of an alternate embodiment of a tubing connector of the present invention.

Referring to FIG. 5, another alternate embodiment of the tubing connector is shown and generally designated 200. The tubing connector 200 has a number of components substantially identical to those of FIG. 4 which are identified in FIG. 5 by the same reference characters as FIG. 4. The tubing connector 200 differs from the tubing connector 10 primarily in the omission of the first shroud 22 from the body 202. In the present configuration of the body 202, a male thread 204 is provided on the outside wall 30 of the central cylinder 18 and a corresponding female thread 206 is provided on the inside wall 66 of the cap 16 proximal to the first end 56. The tubing connector 200 is assembled by screwing the male thread 204 of the central cylinder 18 into the female thread 206 of the cap 16 and compressing the compression member 15 to retain the external end 76 of the catheter 72 in substantially the same manner as described above with respect to the tubing connector 10.

While the forgoing preferred embodiments of the invention have been described and shown, it is understood that alternatives and modifications, such as those suggested and others, may be made thereto and fall within the scope of the invention.

I claim:

1. A tubing connector for a flexible tube comprising:
   a body having a bore extending through said body;
   a tubular member having a body portion positioned in said bore of said body and having an extension portion substantially resistant to elastic deformation extending from said bore of said body; and
   a compression member compressively engaging said body, said compression member having a bore extending through said compression member, wherein said extension portion and a flexible tube fitted over said extension portion are positioned in said bore of said compression member, and wherein said compression member is substantially elastically deformable under compressive force of engagement with said body.

2. The tubing connector of claim 1 wherein said body is substantially resistant to elastic deformation.

3. The tubing connector of claim 1 wherein said body is formed from a nonmetallic material and said tubular member is formed from a metallic material.

4. The tubing connector of claim 1 further comprising a cap fitted over said compression member.

5. The tubing connector of claim 4 wherein said cap has an opening having a larger cross-section than said tubular member and an orifice having a smaller cross-section than said opening and wherein said opening and said orifice are aligned with said bore of said compression member to define a continuous passageway through said cap.

6. The tubing connector of claim 4 wherein said cap is substantially resistant to elastic deformation.

7. The tubing connector of claim 4 further comprising a first coupling element on said cap and a second coupling element on said body for engagement of said cap with said body.

8. The tubing connector of claim 7 wherein said first coupling element is a female thread and said second coupling element is a male thread.

9. The tubing connector of claim 7 wherein said first coupling element is a male thread and said second coupling element is a female thread.

10. The tubing connector of claim 1 further comprising means providing selectively releasable engagement of said body and said compression member.

11. The tubing connector of claim 1 further comprising a coupling element positioned on said body for coupling an adjoining member and said body to provide fluid communication between said tubular member and said adjoining member.

12. A method for fluid communicatively connecting a flexible tube to an adjoining member comprising:
   providing a body having a bore extending through said body;
   threading a portion of a flexible tube through a bore in a compression member, wherein said compression member is substantially elastically deformable under compressive force of engagement with said body;
   providing a body portion of a tubular member positioned in said bore of said body and providing an extension portion of said tubular member extending from said bore of said body, wherein said extension portion is substantially resistant to elastic deformation;
   fitting said portion of said flexible tube over said extension portion; and
   compressively engaging said compression member and said body to compress said compression member against said portion of said flexible tube, wherein said extension portion having said portion of said flexible tube fitted thereover is positioned in said bore of said compression member.

13. The method of claim 12 wherein compressive engagement of said compression member with said body elastically deforms said compression member.

14. The method of claim 12 wherein said body is substantially resistant to elastic deformation.

15. The method of claim 12 wherein said compression member is fitted within a cap substantially resistant to elastic deformation.

16. The method of claim 15 wherein said portion of said flexible tube is threaded through an opening in said cap having a larger cross-section than said tubular member and an orifice in said cap having a smaller cross-section than said opening and wherein said opening and said orifice are aligned with said bore of said compression member.

17. The method of claim 12 further comprising selectively releasably engaging said body and said compression member.

18. The method of claim 12 further comprising coupling said body and an adjoining member to provide fluid communication between said flexible tube and said adjoining member.

19. A method for retaining a flexible tube in a tubing connector without substantially occluding the flexible tube, the method comprising:
   fitting a portion of a flexible tube over a portion of a tubular member;
   threading said portion of said flexible tube through a bore in a compression member, wherein said compression member is substantially elastically deformable under a compressive force;
   providing a body having a bore extending through said body;
   positioning said tubular member in said bore of said body and extending at least a part of said portion of said tubular member and at least a part of said portion of said flexible tube from said bore of said body into said bore of said compression member, wherein said at least a part of said portion of said tubular member is substantially resistant to elastic deformation; and
   compressively engaging said body and said compression member and deforming said compression member to retain said at least a part of said portion of said flexible tube in said bore of said compression member.

20. The method of claim 19 wherein said portion of said flexible tube is fitted over said portion of said tubular member after threading said portion of said flexible tube through said bore of said compression member.

21. The method of claim 19 wherein said portion of said flexible tube is fitted over said portion of said tubular member before threading said portion of said flexible tube through said bore of said compression member.

22. The method of claim 19 wherein said portion of said flexible tube is fitted over said portion of said tubular member after positioning said tubular member in said bore of said body.

23. The method of claim 19 wherein said portion of said flexible tube is fitted over said portion of said tubular member before positioning said tubular member in said bore of said body.

* * * * *